United States Patent
Moissl et al.

(10) Patent No.: US 8,551,342 B2
(45) Date of Patent: Oct. 8, 2013

(54) METHOD OF OPERATING A BLOOD TREATMENT APPARATUS, AND BLOOD VOLUME MONITOR AND BLOOD TREATMENT APPARATUS FOR IMPLEMENTING THE METHOD

(75) Inventors: Ulrich Moissl, Bad Vilbel (DE); Paul Chamney, Herts (GB); Peter Wabel, Darmstadt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 404 days.

(21) Appl. No.: 12/918,734

(22) PCT Filed: Feb. 20, 2009

(86) PCT No.: PCT/EP2009/001228
§ 371 (c)(1),
(2), (4) Date: Nov. 3, 2010

(87) PCT Pub. No.: WO2009/103550
PCT Pub. Date: Aug. 27, 2009

(65) Prior Publication Data
US 2011/0036773 A1    Feb. 17, 2011

(30) Foreign Application Priority Data
Feb. 22, 2008   (DE) .................... 10 2008 010 531

(51) Int. Cl.
*B01D 61/32* (2006.01)
*G05D 7/00* (2006.01)
*G05D 16/00* (2006.01)

(52) U.S. Cl.
USPC ............... 210/739; 210/85; 210/90; 210/97; 210/137; 210/143; 210/258; 210/321.65; 210/645; 210/646; 210/650; 210/741; 604/4.01; 604/6.09; 604/6.11; 604/28; 700/282

(58) Field of Classification Search
USPC ........... 210/645, 646, 650, 739, 741, 744, 85, 210/86, 87, 90, 96.1, 97, 103, 104, 137, 210/143, 252, 257.1, 257.2, 258, 321.65; 604/4.01, 6.09, 6.11, 28; 700/282
See application file for complete search history.

(56) References Cited

U.S. PATENT DOCUMENTS

| | | | |
|---|---|---|---|
| 5,938,938 A | 8/1999 | Bossetto et al. | |
| 2002/0107449 A1 | 8/2002 | Roeher | |

(Continued)

FOREIGN PATENT DOCUMENTS

| | | |
|---|---|---|
| DE | 402 4434 | 2/1992 |
| DE | 198 21534 | 8/1999 |

(Continued)

OTHER PUBLICATIONS

PCT International Search Report for PCT/EP98/001228 mailed on Jul. 16, 2009.

(Continued)

*Primary Examiner* — John Kim
(74) *Attorney, Agent, or Firm* — Kenyon & Kenyon LLP

(57) ABSTRACT

The present invention proposes a method of operating a blood treatment apparatus for the extracorporeal blood treatment of a patient, a blood volume monitor for monitoring an extracorporeal blood treatment of the patient by means of a blood treatment apparatus, and a blood treatment apparatus.

30 Claims, 3 Drawing Sheets

(56) References Cited

U.S. PATENT DOCUMENTS

| | | | |
|---|---|---|---|
| 2006/0047193 A1* | 3/2006 | Zhang | 600/368 |
| 2006/0289342 A1 | 12/2006 | Sugioka et al. | |
| 2010/0016776 A1 | 1/2010 | Roher et al. | |

FOREIGN PATENT DOCUMENTS

| | | |
|---|---|---|
| DE | 19940624 | 11/2000 |
| DE | 100 47421 | 1/2003 |
| DE | 102 30413 | 1/2004 |
| DE | 600 26530 | 9/2006 |
| EP | 0 960 625 | 12/1999 |
| EP | 1192962 | 4/2002 |
| EP | 1226838 | 7/2002 |
| EP | 1 275 407 | 1/2003 |
| EP | 01287838 | 3/2003 |
| EP | 1900384 | 3/2008 |
| WO | WO 93/00938 | 1/1993 |
| WO | WO 01/08723 | 2/2001 |
| WO | WO 2004/004804 | 1/2004 |

OTHER PUBLICATIONS

"BVM—Blood Volume Monitor", Fresenius Medical Care, p. 9 (Undated).

"Replacement of Renal Function by Dialysis, Chapter Hemodialysis machines and monitors", H.D. Polaschegg and N.W. Levin, $5^{th}$ ed. p. 361-364, 397-401. (Undated).

* cited by examiner

METHOD OF OPERATING A BLOOD TREATMENT APPARATUS, AND BLOOD VOLUME MONITOR AND BLOOD TREATMENT APPARATUS FOR IMPLEMENTING THE METHOD

FIELD OF THE INVENTION

The present invention relates to a method of operating a blood treatment apparatus for the extracorporeal blood treatment of a patient. It furthermore relates to a blood volume monitor, as well as a blood treatment.

SUMMARY

In order to remove substances normally subject to excretion via the kidneys from the blood of dialysis patients, blood purification or blood treatment methods such as hemodialysis, hemofiltration, or hemodiafiltration are being employed.

The withdrawal of excess body water, which is generally also necessary in such cases, takes place with the aid of ultrafiltration, generally resulting in a reduction of the patient's blood volume. An overly intense or overly rapid reduction may result in hypotension episodes on the patient's part. The patients' tolerance with regard to a volume reduction is highly variable depending on the individual; in cases of critical patient groups such as, e.g., diabetics, atherosclerosis patients, etc., the incidence of undesirable episodes is clearly increased. The ultrafiltration process and thus the blood volume regulation is therefore critical in terms of safety.

In order to avoid such conditions, apparatuses such as, e.g., the blood volume monitor (BVM) distributed by the company Fresenius Medical Care are known from practice. This monitor is available as an accessory for dialysis apparatus and may be integrated in the latter in the form of an insertion module. The monitor measures the blood volume (BV) and outputs the measurement result as a so-called BVM signal. This signal may indicate a relative blood volume (RBV) as compared to the blood volume at the beginning of the treatment.

Some blood volume monitors enable an automatic feedback between the BVM signal and ultrafiltration control of the dialysis apparatus. This effectively allows avoidance of hypotension episodes by a timely reduction or even interruption of the ultrafiltration as soon as the measured blood volume value approaches particular limits. A drop in the blood volume of the patient being treated to a blood volume that is critical for the latter owing to an excessive withdrawal of liquid by the ultrafiltration will thus not even be reached.

Regarding the feedback between the BVM signal and ultrafiltration control of the dialysis apparatus, there may, however, be cases where the ultrafiltration control is decreased or even stopped on the basis of the BVM signal even though the patient does not exhibit a critical circulatory condition or a respective tendency. As the patient's circulation will be stable in such cases and furthermore remain stable even without any change in the ultrafiltration or ultrafiltration rate, the BVM signal in those cases represents a (measurement) artifact.

It is an object of the present invention to specify another and/or an improved method of operating a blood treatment apparatus for the extracorporeal blood treatment of a patient.

It is another aim of the present invention to propose another and/or an improved blood volume monitor as well as another and/or an improved blood treatment apparatus.

Accordingly, example embodiments of the present invention provide a method of operating a blood treatment apparatus, in particular a dialysis apparatus, for the extracorporeal treatment of a patient's blood, in the execution of which at least one value relating to the blood volume or the evolution thereof (i.e., change over time, as will be explained in more detail below) is obtained.

In the framework of the invention, the expression "value relating to the blood volume" is understood to be a value that is known per se to the skilled person and allows conclusions regarding stability of the patient's circulation. This value may be a figure indicating the patient's absolute blood volume. The value may, however, also indicate a relative blood volume (RBV) which relates to some other blood volume, e.g., a starting volume at the beginning of the treatment. Additional values such as hematocrit etc. are also encompassed by the invention as long as they allow a conclusion as to the blood volume. Other values relate to blood density, blood water content, hemoglobin concentration, but also directly measured values such as the optical density or the propagation time or velocity of ultrasound etc.

In the context of the present invention, the expression "obtaining the value" is understood to be any process which allows a conclusion as to the magnitude of the value or its pertinence to a range of values, or which characterizes the value in some other way. "Obtaining the value" is in particular understood to be the measurement of this value, wherein both direct and indirect measurements are encompassed by the invention. "Obtaining" does, however, also include a calculation of the value based on other known quantities, or any other deduction of the value.

In accordance with the method of the invention, the value of the blood volume is obtained at least at one time of the blood treatment, where this time may be before (in particular immediately preceding) or during the blood treatment. Obtaining the respective current value of the blood volume is possible at a number of times. These times may be separated from each other by predetermined time intervals. They may, however, be adapted in a temporally variable manner in the course of the blood treatment. The intervals may be identical at all times or, on the other hand, different. The value may also be obtained continuously.

In accordance with the invention, a "signal" is understood to be a continuous signal or a non-continuous signal which is either directed to only one means of the blood treatment apparatus or to several means of the blood treatment apparatus. In accordance with the invention, a signal may thus include information which is transmitted to a first means and at the same time to a second means. The kinds of information may be identical or different. Thus one information may be analogous and the other one digital. One information may be of an electrical nature, the other one of an optical nature, etc.

The method of the invention moreover includes obtaining a statement concerning a pressure prevailing in a portion of the blood treatment apparatus or in an extracorporeal circulation, in particular blood pressure, or the evolution thereof. In the framework of the invention, the expression "obtaining" is understood in accordance with the definition given above.

In the framework of the invention, the statement "concerning the pressure prevailing in an extracorporeal circulation" is understood to be either an absolute value, a change of value, a relative value, or any other statement enabling the skilled person to assess relevant pressure events and particularly blood pressure events in one portion of the blood treatment apparatus or in the extracorporeal circulation. The statement may be the (blood) pressure magnitude. "Statement" does, however, also include any specifications of the extracorporeal circulation, such as a rate of flow through tubing sections, a pump speed, or the like.

The method of the invention furthermore includes an examination as to the presence of a coincidence between the blood volume—or at least a value relating to the blood volume at at least one point of time or its evolution across at least two points of time of the blood treatment—and the blood pressure—or a statement concerning a pressure prevailing in a portion of the blood treatment apparatus or in an extracorporeal circuit, in particular a blood pressure—or the respective evolutions thereof.

In terms of the invention, an "examination as to the presence of a coincidence" is understood to be an analysis, check, observation or the like, each having the objective of recognizing a possibly existing coincidence within the meaning of the present invention.

In terms of the invention, an examination may quite generally be understood to be a targeted observation or acquisition of information. Preferably, an examination serves for recognition of a relation between events or developments.

For the purpose of examining within the meaning of the present invention, mathematical models or algorithms, in particular threshold value models, trend analyses or the like are preferably employed. Besides calculations of the kind stated in the foregoing, examination may also take part by way of a pure observation together with a subjective evaluation of the observation.

The expression "coincidence" as presently used encompasses—without being restricted thereto—a synchronous occurrence of two events.

The expression coincidence furthermore encompasses a causal relation, irrespective of whether it manifests simultaneously or at a temporal offset. Coincidence moreover encompasses both a positive correlation and a negative correlation.

Advantages that may be achieved by the utilization of the method of the invention include, for instance, the possibility of identifying artifacts in the blood volume measurement based on an examination as to the presence of coincidences. If artifacts are present, interventions in the blood treatment that are not necessary but are carried out in practice owing to the unrecognized presence of an artifact—such as to reduce a filtration capacity, output an alarm or the like—may be omitted without negative consequences particularly to the patient. In addition, identification of a coincidence may cause the performance of corrective method steps.

In a preferred example embodiment, the method of the invention furthermore includes outputting at least a first signal for controlling or regulating the blood treatment apparatus, and in particular for controlling or regulating an ultrafiltration or a rate of ultrafiltration. In outputting the signal, the obtained blood volume value is reflected. In the context of the present invention this is understood to mean, e.g., that a control signal output to the blood treatment apparatus at a time of a low blood volume causes the blood treatment apparatus to reduce the ultrafiltration capacity or rate, respectively, in comparison with an ultrafiltration capacity or rate that is output at a time when a higher blood volume value is obtained. In this context it is noted that "outputting" the signal equally signifies "generating"—i.e., determining, calculating, etc. of the signal.

In this example embodiment, the method of the invention moreover includes an adaptation of the first signal which is output for controlling or regulating the blood treatment apparatus and in particular the ultrafiltration rate, wherein the obtained statement concerning the prevailing pressure, and particularly blood pressure, is reflected in this signal.

Reflecting the obtained statement concerning the pressure or blood pressure results in a first signal which controls or regulates the blood treatment apparatus in such a manner that the ultrafiltration capacity and/or rate is lowered or reduced, for instance, so that the patient's circulation is efficiently prevented from reaching critical conditions.

The adaptation of the first signal may furthermore take place in such a manner that in addition to outputting first information, second information for utilization by the blood treatment apparatus is also output, with the second information bringing about a reduction of the ultrafiltration capacity and/or rate. Thus even a critical RBV signal may be output without a change while ultrafiltration may nevertheless be stopped by a second signal which does, e.g., stop the filtration pump and is output additionally in the event of critical RBV signals.

It should be noted that in the context of the present invention, the skilled person will regularly have to replace the expression "control" with "regulation" (or closed-loop control)—the latter of which is equally encompassed by the present invention—when this is discernible to the skilled person based on the present application and based on his technical learning. In the context of the present invention it is moreover a general rule that any mention of ultrafiltration or ultrafiltration capacity and control or regulation thereof also designates the ultrafiltration rate—and vice-versa—as long as the skilled person recognizes an applicability of the statement to the respective other expression.

In a further preferred embodiment, a method is proposed which includes changing the magnitude of the output first signal for controlling the blood treatment apparatus so as to reflect the obtained statement, in particular by adding a pressure-proportional value to the signal. The magnitude of the signal may, however, also be reduced in the process. The signal may thus be reduced down to a magnitude at which the blood treatment means cancels its effect so that, for instance, filtration is suppressed.

The method of the invention includes, in another embodiment of the invention, outputting at least a second signal that is independent of the first signal, while reflecting the obtained statement. The signal may in particular be a signal which brings about an at least temporal or transient interruption of a control or regulation of the blood treatment, and in particular of an ultrafiltration taking place, to the obtained value.

In another, in turn further preferred embodiment, the method of the invention includes outputting a signal for performing an at least temporarily constant blood treatment and in particular an at least temporarily constant ultrafiltration. This signal may be the modified first signal, the modified second signal, or a third signal which is independent of the first and second signals.

The at least temporary operation of the blood treatment apparatus at a constant ultrafiltration rate and/or capacity brings about a deactivation of the ultrafiltration control or regulation. Safety mechanisms may, however, preferably be provided in such a manner that changes of the pressure/blood pressure in the extracorporeal circulation or in the portion of the blood treatment apparatus, which come about due to settings changed by the operator or due to known and intended circumstances and which are intended to result in a change of the ultrafiltration rate or capacity, will not result in an adaptation of the signal. Rather, in such cases ultrafiltration is to be stopped or reduced as is usual in practice. In such a case, preferably outputting a warning signal may additionally take place.

The statement concerning the pressure/blood pressure prevailing in a portion of the blood treatment apparatus or in an extracorporeal circulation may, in an again further preferred example embodiment, result from measuring the pressure/ blood pressure in the extracorporeal circulation, in particular in a venous section thereof. The measured pressure/blood pressure may then be used in the form of an absolute value, a relative value, in a temporal derivation, or in some other manner.

As is provided by an again further preferred example embodiment of the invention, the relative blood volume for obtaining a statement may be measured through the intermediary of the blood volume.

A further preferred embodiment of the method of the invention provides outputting or generating a RBV signal while reflecting the obtained statement for controlling or regulating the blood treatment apparatus.

By means of the method of the invention it is advantageously possible to omit a reduction of ultrafiltration in the event of dropping values relating to the blood volume (such as a drop of the RBV signal) that are inherently of relevance for a control or regulation but not accompanying or presaging a critical circulatory condition, and which must therefore be designated measurement artefacts. This saves time which the patient has to set aside for the treatment, including all the respective advantages known to the skilled person.

The object of the invention is also achieved through a blood volume monitor having the features described herein and through a blood treatment apparatus having the features described herein. By means of the blood volume monitor of the invention, and also by means of the blood treatment apparatus of the invention, all of the above mentioned advantages may be obtained undiminished. In order to avoid repetitions, reference is therefore expressly made to the above discussion and representation.

The present invention shall in the following be explained in more detail by way of an embodiment that is represented in the drawings.

DETAILED DESCRIPTION

Figure 1:
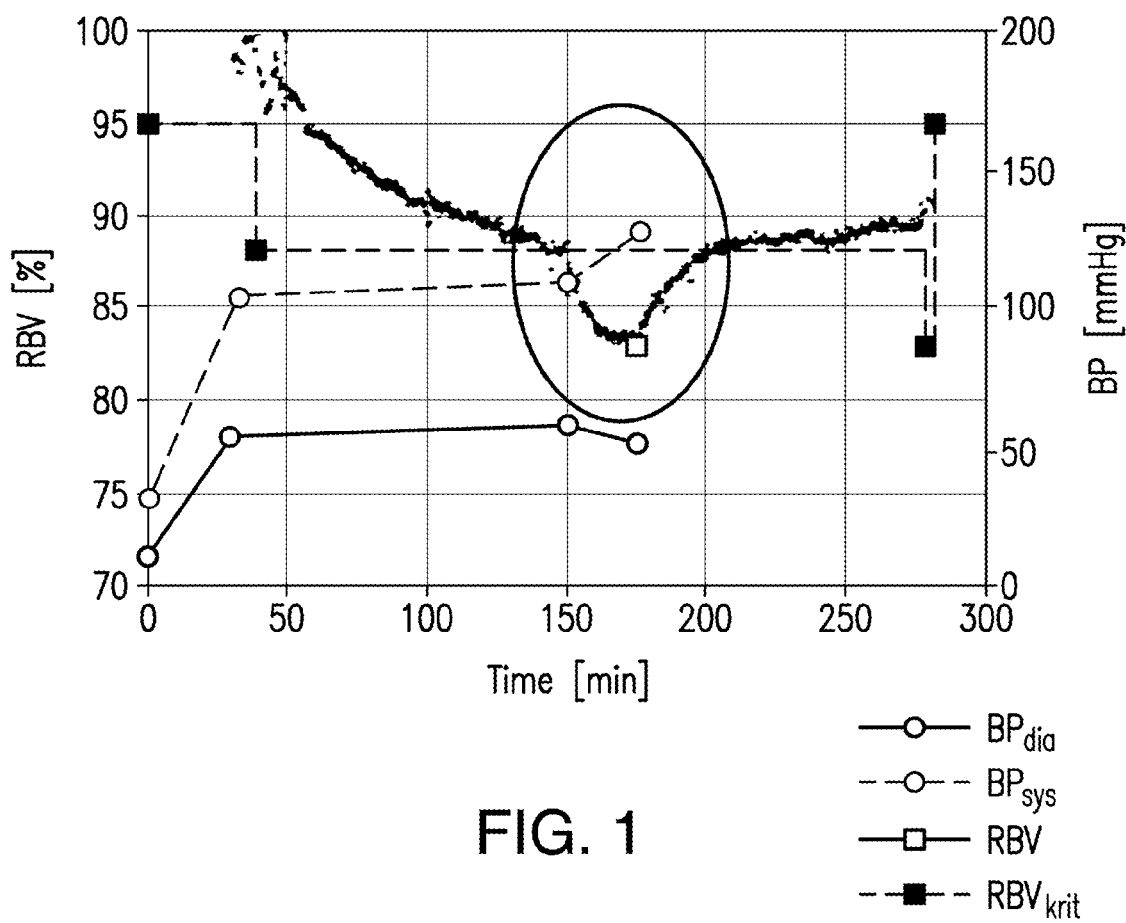
FIG. 1 shows a RBV signal and blood pressures of a patient during a dialysis treatment vs. time.

FIG. 1 shows both the relative blood volume, RBV, expressed as a percentage [%], and the blood pressure, expressed in mmHg, versus the temporal evolution of a patient's blood treatment graded in minutes. The systolic blood pressure is designated by $BP_{sys}$, and the diastolic blood pressure by $BP_{dia}$. In FIG. 1 the critical relative blood volume $RBV_{krit}$ is moreover represented. If the RBV signal drops below this critical value, then ultrafiltration is lowered or deactivated in the present example. It is noted, however, that the represented example generally relates to the blood pressure. As was explained further above, however, another pressure may also be measured. In accordance with the above explanation, the RBV measurement is here also representative for the measurement of some other blood parameter.

As is shown by FIG. 1, the RBV signal in the example represented there suddenly drops exponentially by about 5% at the time t=150 min, to only increase again after 20 to 30 minutes. As may also be seen in FIG. 1, however, the strong drop of the RBV signal is not accompanied by a drop of the blood pressure; both the systolic blood pressure $BP_{sys}$ and the diastolic blood pressure $BP_{dia}$ remain substantially unchanged during the strong RBV drop. Accordingly, a critical circulatory condition does in any event not exist in the time range enclosed by a bold line.

One of the following causes might be responsible for the RBV drop represented in FIG. 1:

1) Refilling from the interstice to the vascular system changes owing to ingestion of food (for instance, the patient taking breakfast during the treatment) or an alteration of the filtration pressures.
2) Fahraeus-Lindquist effect: mobilization of blood compartments having different plasma water concentrations. For example, owing to the block flow of erythrocytes, the hematocrit HCT in the narrower capillaries is reduced in comparison with the larger arteries. If a previously inactive capillary bed is added to the circulating blood volume, blood rich in plasma water flows into the capillary, whereby the circulating hematocrit detected in the course of the ultrasonic measurement by the blood volume monitor BVM results in an attenuation of the RBV signal.

During a RBV-based ultrafiltration regulation in which the RBV value must not cross a critical lower limit $RBV_{krit}$, the sudden RBV drop would bring about a significant reduction of the ultrafiltration, partly even its deactivation for approx. 15-40 minutes, which has a negative impact on the duration of dialysis or the total ultrafiltration volume, respectively, or on the purification capacity.

Figure 2:
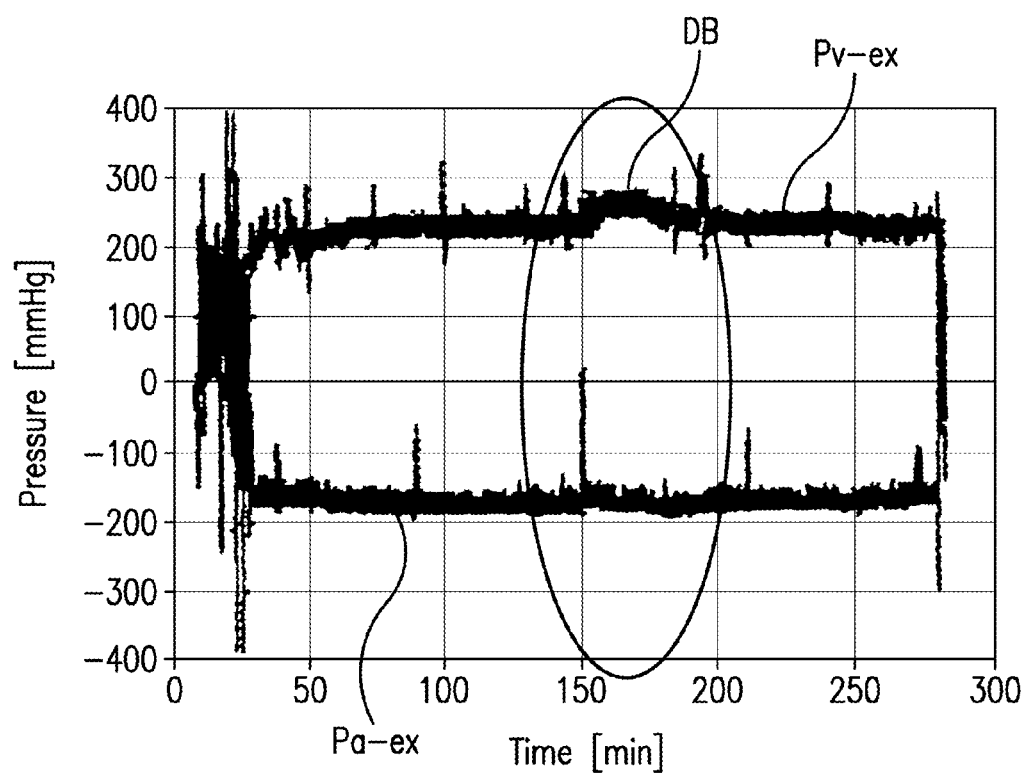
FIG. 2 shows the arterial and venous pressure signal in the extracorporeal circulation.

As may be seen in FIG. 2 representing the arterial pressure signal $P_{a-ex}$ and the venous pressure signal $P_{v-ex}$ of the extracorporeal circulation, the RBV drop occurring at the time t=150 min and already shown in FIG. 1 is accompanied by a change particularly in the venous pressure signal $P_{v-ex}$. This change is well distinguishable in the area enclosed by the bold line. It manifests in the venous pressure signal as a "pressure bump", designated by DB in FIG. 2.

Upon identification of such a pressure bump DB it is an option in accordance with the invention, for example, to correct the RBV signal. This may be carried out in one example embodiment of the invention by adding a pressure-proportional and optionally patient-specific value to the RBV signal. Another possible course of action upon identification of such a pressure bump is to deactivate the ultrafiltration regulation for the duration of the pressure bump. During the time in which the ultrafiltration regulation is deactivated, it is possible to auxiliarly continue with a constant ultrafiltration rate.

Advantageously, in each possible correction of the RBV signal or of the transient change of the ultrafiltration rate it may be ensured that pressure changes caused, e.g., by flow changes will not be used for the identification of artefacts. In this case a correction of the RBV signal would not take place.

Figure 3:
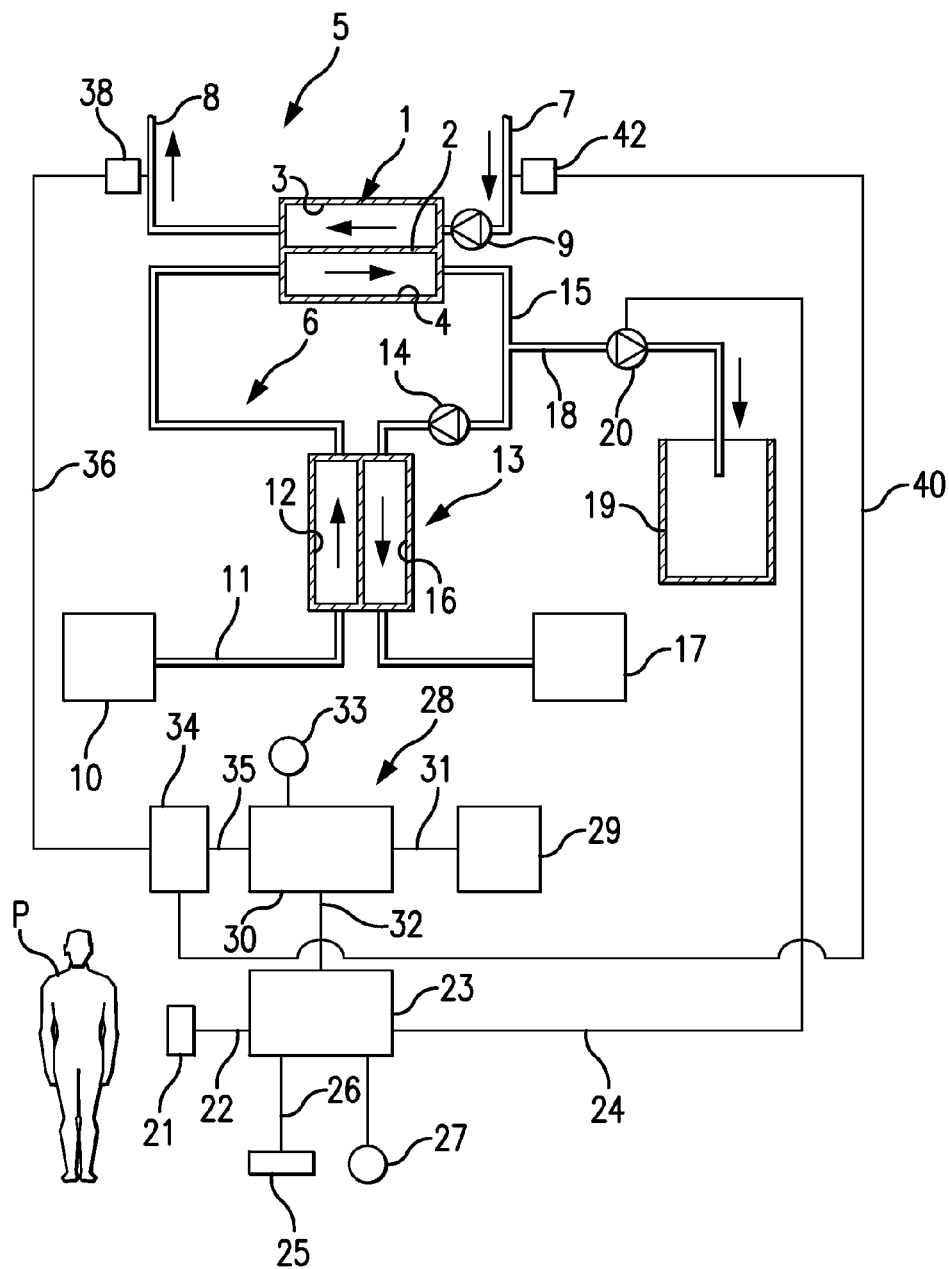
FIG. 3 shows in a schematically simplified representation a blood treatment apparatus in accordance with the invention.

FIG. 3 shows the essential components of a hemodiafiltration apparatus as an example of a blood treatment apparatus of the invention, together with a blood volume monitor of the invention, in schematic representation. The blood volume monitor may be an integral component of the blood treatment apparatus (here: of the hemodiafiltration apparatus) or a separate unit which is connected to an already existing blood treatment apparatus.

The hemodiafiltration apparatus of FIG. 3 includes a dialyzer 1 subdivided by a semi-permeable membrane 2 into a blood chamber 3 and a dialysis fluid chamber 4. The blood chamber 3 is positioned in an extracorporeal blood circulation 5 while the dialysis fluid chamber 4 is positioned in a dialysis fluid circuit 6. From a patient P a blood feed line 7 leads to an inlet to the blood chamber 3 of the dialyzer 1, and from an outlet of the blood chamber 3 a blood discharge line 8 leads back to the patient P. A blood pump 9 is positioned in the blood feed line 7.

A dialysis fluid feed line 11 leads from a dialysis fluid source 10 to the inlet to a first balancing chamber 12 of a balancing unit 13 and from the outlet of the latter to the inlet of the dialysis fluid chamber 4 of the dialyzer 1.

A dialysis fluid discharge line 15 leads from an outlet of the dialysis fluid chamber 4 to a second balancing chamber 16 of the balancing unit 13 and from the outlet thereof to a discharge 17. A dialysis fluid pump 14 is positioned in the dialysis fluid discharge line 15 upstream from the balancing unit 13.

Upstream from the second balancing chamber 16 of the balancing unit 13, an ultrafiltrate line 18 branches from the dialysis fluid discharge line 15 and leads to a discharge 19 that may be identical with the discharge 17. An ultrafiltrate pump 20 is positioned in the ultrafiltrate line 18 in order to withdraw the ultrafiltrate.

In the inactive state of the ultrafiltrate pump 20, the balancing unit 13 prevents a net exchange of fluid between primary and secondary circuits 5, 6. Ultrafiltration does not take place under these circumstances. Ultrafiltration is only put into effect by turning on the ultrafiltrate pump 20 which withdraws liquid from the dialysis fluid chamber 4 of the dialyzer 1 in a controlled manner (ultrafiltration).

The blood treatment apparatus including the blood volume monitor 28 is provided with a measuring unit 21 for determining the patient's P blood volume BV during the blood treatment. The measuring unit 21 is connected via a data line 22 to a control unit 23 which is connected via a data line 24 to the ultrafiltrate pump 20. In general, it is sufficient for the blood volume monitor 28 of the invention or for carrying out the method of the invention, respectively, if the measuring unit 21 furnishes relative indications concerning the blood volume of the patient P, such as, e.g., indications concerning the water content in the extracorporeal blood of the patient P, e.g., in line 7. It is also possible to measure other measurement quantities correlated with the relative blood volume, such as, e.g., a hemoglobin or protein concentration. In such case an ultrasonic sensor may be employed. The skilled person is aware of how to proceed in such measurements or determinations.

For the purpose of inputting a total ultrafiltrate volume $UFV_{ges}$ to be withdrawn during overall duration of treatment, and for the purpose of inputting the treatment duration UFT and other parameters (optionally patient-specific parameters), an input unit 25 is provided which is connected to the regulation unit 23 via a data line 26. The regulation unit 23 adjusts the ultrafiltration rate UFR(t) of the ultrafiltrate pump 20 as a function of the blood volume BV of the patient P as measured by the measuring unit 21, such that the predetermined total ultrafiltrate volume $UFV_{ges}$ will be withdrawn during the predetermined treatment duration UFT (blood volume regulation). To this end, the regulation unit 23 is provided with a corresponding regulation algorithm.

By operating a switch 27 it is possible to deactivate the regulation unit 23 and proceed to manually set the ultrafiltration rate.

The blood volume monitor 28 prevents a risk to the patient P in the event of a faulty blood volume regulation. The blood volume monitor 28 includes a calculating unit 29 and a monitoring unit 30 which communicate with each other via a data line 31. The monitoring unit 30 is connected to the regulation unit 23 via a data line 32.

The calculating unit 29 of the blood volume monitor 28 may determine an upper limit for the ultrafiltration rate $UFR_{lim}$ based on the predetermined total ultrafiltrate volume $UFV_{ges}$ and the predetermined treatment duration UFT.

The blood volume monitor 28 further includes means 34 for adapting the RBV signal while reflecting the magnitude of the blood pressure in the extracorporeal circulation 5, wherein the means 34 is connected to the blood volume monitor 28 via a data line 35. The means 34 is connected, via a measurement line 36 for measuring the magnitude of the blood pressure with the aid of a pressure sensor 38 having an arbitrary configuration (e.g., a pressure dome or the like) in the extracorporeal circulation 5, with the venous leg thereof (blood discharge line 8). The represented measurement line 40, which equally includes a pressure sensor 42 that may have a same configuration as the pressure sensor 38, may be provided in addition to or instead of the measurement line 36. Instead of the measurement in the venous leg—or in addition thereto—a measurement may also be provided in the arterial leg (blood feed line 7) of the extracorporeal blood circulation 5.

The following is a description of a possible and purely exemplary manner of realization of the method of the invention which may be carried out by means of the apparatus discussed in the drawings. The following method may take place repeatedly and in particular regularly during the blood treatment (e.g., once a minute) and may include the following steps:

The RBV signal of, e.g., the past half hour is approximated linearly or exponentially and thus smoothed. Alternatively, low-pass filtering or any other suitable filtering of the RBV signal may take place. In the following, the smoothed signal is referred to as an approximation. The current RBV signal is compared to the approximation that was interpolated or extrapolated for the current point in time.

If the comparison shows that a rapid, intense drop of the RBV exists (one criterion for this might be, for instance, a RBV deviation between current value and approximation in excess of, e.g., −3%, or a particular drop such as, e.g., −3% taking place within a maximum of 5 minutes), then the arterial and venous pressures in the tubing system are examined. Here, too, a comparison of the current values with corresponding pressure approximations over the past 5 to 10 minutes, e.g., may take place, where an examined is performed as to whether a rapid, distinct arterial and venous pressure increase is present; i.e., an examination is performed whether or not the current pressure deviates from its approximation within a short time period (e.g., within 5, 10, 20, 30, 40, 50, 60 seconds or 1, 2, 3, 4, or 5, 6, 7, 8, 9, 10, 11, 12, 13, 14, 15 minutes or more). One criterion for the positive case might be, for instance, the arterial pressure deviating from its approximation by more than 10 mmHg (more than 5 or 15 mmHg and intermediate values and further values are equally conceivable) and the venous pressure deviating from its approximation by more than 5 mmHg (more than 3, 4, 6, 7, 8, 9, or values between 10 or 15 and further values are equally conceivable).

If the criterion is satisfied, i.e., if the current pressure deviates from its approximation, then a RBV artefact owing to a change of position (breakfast, etc.) is conjectured, the RBV regulation is deactivated, and a constant UF rate is set. This setting may be adhered to until identical or comparable effects take place in a reversed form or direction (e.g., a if the RBV signal increases, in particular suddenly, upwardly with a concurrent reduction of the blood pressures, or if the previous RBV starting value preceding the breakfast-related drop is reached). In this event the regulation may again be activated.

Although in this configuration the current RBV measuring point or BP measuring point is examined as to sudden, intense deviations, it is also within the scope of the invention to carry out a prediction of the RBV signal by extrapolating the approximation to future values. This provides the advantage that a predictive regulation ("prediction") may react more quickly to some events, which may be of particular advantage if the respective manipulated variable changes its magnitude or form only slowly, or is sluggish.

The present invention proposes a method of operating a blood treatment apparatus for the extracorporeal blood treatment of a patient, a blood volume monitor for monitoring an extracorporeal blood treatment of the patient by means of a blood treatment apparatus, and a blood treatment apparatus.

The invention claimed is:

1. A method of operating a blood treatment apparatus for the extracorporeal blood treatment of a patient (P), comprising:
   obtaining a value (RBV) relating to (a) the blood volume at least at one point of time of the blood treatment or (b) a change in the blood volume through at least two points of time of the blood treatment;
   obtaining a statement ($P_{a-ex}$, $P_{v-ex}$) concerning (a) a pressure prevailing in a portion of the blood treatment apparatus or in an extracorporeal circulation or (b) a change in the pressure prevailing in the portion of the blood treatment apparatus or in the extracorporeal circulation;
   determining the presence of a coincidence between the change in the blood volume and the change in the pressure, the determination being based on (a) the value (RBV) and the statement ($P_{a-ex}$, $P_{v-ex}$) and/or (b) a change in the value (RBV) and a change in the statement ($P_{a-ex}$, $P_{v-ex}$).

2. The method according to claim 1, wherein the pressure is a blood pressure.

3. The method according to claim 1, further comprising:
   outputting a first signal for controlling the blood treatment apparatus, the first signal reflecting (a) the obtained value (RBV) or (b) the change in the obtained value (RBV); and
   adapting the first signal to additionally reflect the obtained statement ($P_{a-ex}$, $P_{v-ex}$).

4. The method according to claim 3, wherein the first signal is for controlling a rate or capacity of ultrafiltration of the blood treatment apparatus.

5. The method according to claim 3, further comprising:
   changing the magnitude of the first signal for controlling the blood treatment apparatus while the first signal reflects (a) the obtained statement ($P_{a-ex}$, $P_{v-ex}$) or (b) the change in the obtained statement ($P_{a-ex}$, $P_{v-ex}$).

6. The method according to claim 5, wherein the magnitude is changed by adding a pressure-proportional value to the first signal.

7. The method according to claim 3, further comprising:
   outputting a second signal reflecting (a) the obtained statement ($P_{a-ex}$, $P_{v-ex}$) or (b) the change in the obtained statement ($P_{a-ex}$, $P_{v-ex}$).

8. The method according to claim 7, wherein the second signal is for at least temporarily interrupting a control of the blood treatment.

9. The method according to claim 1, further comprising:
   outputting a signal for performing an at least temporarily constant blood treatment.

10. The method according to claim 1, further comprising:
    measuring the pressure in the extracorporeal circulation to obtain the statement ($P_{a-ex}$, $P_{v-ex}$).

11. The method according to claim 10, wherein the pressure is a blood pressure.

12. The method according to claim 10, wherein pressure is measured in a venous portion of the extracorporeal circulation.

13. The method according to claim 1, further comprising:
    measuring the relative blood volume (RBV) to obtain the value (RBV) relating to (a) the blood volume at least at one point of time of the blood treatment or (b) a change in the blood volume through at least two points of time of the blood treatment.

14. A blood volume monitor for monitoring an extracorporeal blood treatment of a patient via a blood treatment apparatus, said blood volume monitor comprising:
    means for obtaining a value relating to (a) the blood volume (BV) at least at one point of time of the blood treatment or (b) a change in the blood volume through at least two points of time of the blood treatment; and
    means for obtaining a statement ($P_{a-ex}$, $P_{v-ex}$) concerning (a) a pressure prevailing in a portion of the blood treatment apparatus or in an extracorporeal circulation or (b) a change in the pressure prevailing in the portion of the blood treatment apparatus or in the extracorporeal circulation; and
    a control unit configured to determine the presence of a coincidence between a change in the blood volume and a change in the pressure, using (a) the value (RBV) and the statement ($P_{a-ex}$, $P_{v-ex}$) and/or (b) a change in the value (RBV) and a change in the statement ($P_{a-ex}$, $P_{v-ex}$).

15. The blood volume monitor according to claim 14, wherein the pressure is a blood pressure.

16. The blood volume monitor according to claim 15, further comprising:
    a regulation unit configured to output a first signal reflecting the obtained value (RBV) for controlling the blood treatment apparatus; and
    means for adapting the first signal to additionally reflect the obtained statement ($P_{a-ex}$, $P_{v-ex}$) concerning (a) the pressure prevailing in a portion of the blood treatment apparatus or in an extracorporeal circulation or (b) the change in the pressure prevailing in the portion of the blood treatment apparatus or in the extracorporeal circulation.

17. The blood volume monitor according to claim 16, wherein the first signal is for controlling a rate or capacity of ultrafiltration of the blood treatment apparatus.

18. The blood volume monitor according to claim 16, further comprising:
    means for changing the magnitude of the output first signal for controlling the blood treatment apparatus to reflect (a) the obtained statement ($P_{a-ex}$, $P_{v-ex}$) or (b) the change in the obtained statement ($P_{a-ex}$, $P_{v-ex}$).

19. The blood volume monitor according to claim 18, wherein the magnitude is changed by adding a pressure-proportional value to the first signal.

20. The blood volume monitor according to claim 16, further comprising:
    means for outputting a second signal reflecting (a) the obtained statement ($P_{a-ex}$, $P_{v-ex}$) or (b) the change in the obtained statement ($P_{a-ex}$, $P_{v-ex}$).

21. The blood volume monitor according to claim 20, wherein the second signal is for at least temporarily interrupting a control of the blood treatment.

22. The blood volume monitor according to claim 14, further comprising:
    means for outputting a signal for performing an at least temporarily constant blood treatment.

23. The blood volume monitor according to claim 15, further comprising:

a measurement line configured to measure the blood pressure in the extracorporeal circulation.

24. The blood volume monitor according to claim 23, wherein the measurement line is configured to measure the blood pressure in a venous portion of the extracorporeal circulation.

25. The blood volume monitor according to claim 14, further comprising:
a measurement unit configured to measure the relative blood volume (RBV).

26. A blood treatment apparatus, comprising:
a blood volume monitor according to claim 14; and
a dialysis apparatus configured to accommodate the blood volume monitor.

27. The blood treatment apparatus according to claim 26, wherein the dialysis apparatus is configured to accommodate a blood tubing system for the extracorporeal blood circulation.

28. The blood treatment apparatus according to claim 26, further comprising a blood tubing system for the extracorporeal blood circulation.

29. The blood treatment apparatus according to claim 26, wherein the dialysis apparatus is configured to accommodate a hemodialyzer.

30. The blood treatment apparatus according to claim 26, wherein the dialysis apparatus includes a hemodialyzer.

* * * * *

UNITED STATES PATENT AND TRADEMARK OFFICE
CERTIFICATE OF CORRECTION

PATENT NO.        : 8,551,342 B2
APPLICATION NO. : 12/918734
DATED             : October 8, 2013
INVENTOR(S)       : Moissl et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 476 days.

Signed and Sealed this
Fifteenth Day of September, 2015

Michelle K. Lee
*Director of the United States Patent and Trademark Office*